United States Patent [19]
Gupte et al.

[11] Patent Number: 5,462,744
[45] Date of Patent: Oct. 31, 1995

[54] TRANSDERMAL SYSTEM FOR THE ADMINISTRATION OF PHARMACOLOGICAL COMPOUNDS UNDER PH-CONTROLLED CONDITIONS

[75] Inventors: Arun R. Gupte, Ingelheim am Rhein; Uwe Rohr, Gau Algesheim; Bernd Zierenberg, Bingen, all of Germany

[73] Assignee: Boehringer Ingelheim KG, Ingelheim am Rhein, Germany

[21] Appl. No.: 148,796

[22] Filed: Nov. 8, 1993

Related U.S. Application Data

[63] Continuation of Ser. No. 741,498, Jul. 24, 1992, abandoned.

[30] Foreign Application Priority Data

Nov. 29, 1990 [DE] Germany .......................... 39 39 703.3

[51] Int. Cl.⁶ .................................................. A61F 13/00
[52] U.S. Cl. .......................................... 424/448; 424/449
[58] Field of Search ....................................... 424/448, 449

[56] References Cited

U.S. PATENT DOCUMENTS

| 4,801,458 | 1/1989 | Hidaka | 424/443 |
| 4,830,856 | 5/1989 | Peppers | 424/449 |
| 5,000,956 | 3/1991 | Amkraut | 424/434 |
| 5,116,621 | 5/1992 | Oji | 424/445 |

FOREIGN PATENT DOCUMENTS

| 0197504 | 10/1986 | European Pat. Off. . |
| 2174605 | 11/1986 | United Kingdom . |
| 8700042 | 1/1987 | WIPO . |

*Primary Examiner*—D. Gabrielle Phelan
*Attorney, Agent, or Firm*—R. P. Raymond; M-E. M. Devlin; A. R. Stempel

[57] ABSTRACT

The invention relates to an improved transdermal administration of pharmacologically active compounds.

4 Claims, 5 Drawing Sheets

TRANSDERMAL SYSTEM FOR THE ADMINISTRATION OF PHARMACOLOGICAL COMPOUNDS UNDER PH-CONTROLLED CONDITIONS

This is a continuation, of application Ser. No. 07/741,498, filed Jul. 24, 1992, now abandoned.

The invention relates to an improved transdermal system in the form of a plaster for the administration of pharmacologically active substances under skin surface-pH-controlled conditions.

The transdermal administration of pharmacologically active compounds using transdermally therapeutic systems has been known in the prior art for some time. Suitable plasters for this purpose are disclosed for example in U.S. Pat. Nos. 3,558,122 and 3,558,123. Although in these and numerous subsequent patent applications a number of active substances are shown to be suitable, it has been found in practice that unexpected problems may occur when they are used on patients even if tests carried out in vitro have already demonstrated that the plaster containing the active substance will release the active substance in sufficient quantities.

However, when the theory was put into practice on humans, the sufficiently high or constant blood level values expected could not be achieved. Thus, for example, clenbuterol is used orally in the form of tablets or syrups as a β-sympathomimetic for treating bronchial asthma. Contrary to expectation, the transdermal administration of clenbuterol has not hitherto resulted in constant blood level values.

Figure 1:
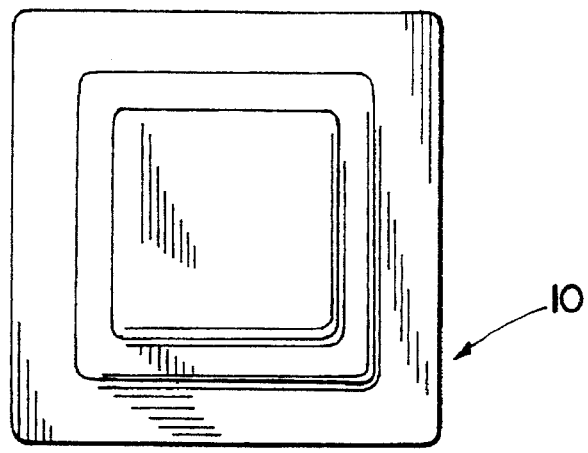
FIG. 1 show a front view of a transdermal patch.

It has been found, surprisingly, that the flux rate for the active substance in the transdermal administration of clenbuterol can be crucially improved if the pH of the skin surface is maintained at a constant level between 6.0 and 8.5.

The flux rate of an active substance through the skin is defined as the quantity of active substance per unit of area of the skin and per unit of time and is normally given in [μg/cm$^2$.h]. The flux rate for clenbuterol reaches a maximum in the pH range specified above, but decreases sharply at higher and lower pH levels.

The pH level of the skin surface differs between individual people and at different times. A pH level of 5.5 to 6.0, taken as standard, will fluctuate in individual cases between pH 4.5 and 8.0 and will depend on a number of different factors. Fluctuations in the pH level may be caused on the one hand by the plaster itself and on the other hand by the active substance. As can be seen from FIG. 9 the flux rate of clenbuterol is reduced drastically outside the pH range specified, with the result that it is no longer guaranteed that the skin will be sufficiently permeable for clenbuterol.

The invention further relates to transdermal systems which make it possible to achieve a constant pH level on the skin and thus allow active substances to diffuse through the skin in the range of their maximum flux rate. According to the invention, this establishes the optimum flux rate for the active substance in patients, irrespective of the inherent pH of the skin.

Such systems may be constructed by having, on the side which comes into contact with the skin, a chemical substance (additive) which buffers the pH value on the surface of the skin in the desired area. Obviously, the substances or mixtures of substances involved must be pharmacologically acceptable. For achieving a predetermined pH value on the skin, it is appropriate to use additives such as, for example, weak bases, weak acids, organic and inorganic salts which form a buffer system with the skin surface, or buffer mixtures (buffer systems).

The quantity of additives should not be too small, so as to ensure that the pH value on the surface of the skin can be adjusted to the desired level for the entire period of time that the plaster is worn.

The quantity of additive is generally between 2 and 10% by weight, based on the weight of the active substance reservoir of the transdermal system, whilst a range between 4 and 6% by weight is preferred.

This quantity of additive is sufficient to adjust the pH of the skin to a predetermined level for a period of 1 to 7 days.

The advantages of such an adjustment of the pH value are, on the one hand, that basic active substances which set up a basic pH level on the skins surface are able to shift the pH of the skin into the acid range by the addition of acid salts. In this way, the acceptability of transdermal systems can be improved substantially, since the growth of bacteria in the acid pH range is substantially reduced.

Another advantage of adjusting the pH on the surface of the skin is the fact that slightly acidic or basic active substances will form a buffer system by the addition of suitable salts and a defined pH will be obtained, so that fluctuations in the pH of the skin surface can be balanced out.

Suitable salts or weak acids which are suitable as additives for adjusting the pH include the following for example:

Disodium hydrogen phosphate, sodium dihydrogen phosphate, sodium acetate, potassium dihydrogen phosphate, sodium carbonate, sodium hydrogen carbonate, boric acid, sodium borate, citric acid, sodium or potassium citrate, monocalcium orthophosphate (Ca(H$_2$PO$_4$)$_2$), potassium hydrogen phosphate, dipotassium hydrogen phosphate, tartaric acid, potassium or sodium tartrate, sodium hydrogen phthalate.

Buffer systems and buffer mixtures with which a pH value of between 3 and 10 can be achieved are sufficiently well known from the prior art.

The following are examples of active substances the diffusion characteristics of which can be changed by adjusting the pH:

Physostigmine, clonidine, fentanyl, MR 2264 (N-(2-methoxyethyl)-noroxy-morphone), ephedrine, nicotinicacidamide, clenbuterol, pramipexol, lisuride, terbutaline, salbutamol, hexoprenaline, insulin, vasopressin, atrial natriuretic peptide (ANP).

The advantages and findings according to the invention can also be applied to other active substances occurring in the form of weak basis or weak acids.

The plaster according to the invention may also advantageously be used to make the pH of the skin surface slightly acidic (pH=5.5 to 6.9), so as to avoid undesirable bacterial growth and possible skin irritations resulting from it.

Neutral molecules the flux rate of which is unaffected or only slightly affected by the pH of the skin are particularly suitable for this purpose e.g. nitroglycerine.

Transdermal systems suitable for use according to the invention for adjustment of the pH value are known from the prior art. Generally, they are matrix systems of one of the polymers or copolymers listed below.

Polymethacrylate, polyvinylpyrrolidone, ethylzellulose, hydroxypropylmethylzellulosephthalate, polyvinylalcohol or copolymers thereof with vinyl laurate or maleic acid, vinyl acetate or copolymers thereof with vinyllaurate, or maleic acid, vinyl acetate or copolymers thereof with vinyl laurate or maleic acid, polyvinylether, butyl rubber and polycaprolactam.

Preferred polymers and copolymers are those produced by emulsion polymerisation. With polymers of this kind, it is known that the release of active substance can be adjusted by varying the particle size of the polymer particles, by varying the layer thickness in the range between 40 and 200 μm, preferably up to 140 μm, and by varying the glass transition temperature.

The particle size relates to the particle diameter of the polymeric material after it has been produced and may be up to 500 μm. The particle size (diameter) can be adjusted depending on the conditions of polymerisation. A reduction in the particle size results in an increase in the rate of release.

The glass transition temperature can be adjusted by changing the monomer composition and is, for example, between −20° and +80° C., preferably between −20° and +40° C., particularly preferably between −10° and +30° C. An increase in the glass transition temperature is connected with a lowering of the rate of release.

Using the emulsion polymerisation method, the following polymers may be prepared, for example PVC, polylactides, polystyrene, polyvinylacetate, polybutadiene, polyacrylnitrile, polyvinylester, polyvinylether and copolymers thereof. Emulsion polymerised copolymers of methyl and/or ethyl esters of acrylic ad methacrylic acid are preferred. The molecular weight of the emulsion polymers should be between $10^4$ and $10^7$. The carrier material may be recovered as a solid, e.g. by freeze drying, with the particles of polymer retaining their shape and size.

Matrix systems for transdermal administration consist of a backing layer which contains the active substance, a reservoir containing the active substance (active substance matrix store) and means for securing it to the skin.

The release of active substance is controlled either by a suitable choice of the polymer matrix—as disclosed for example in European Patent 86997—or by means of suitable membranes, as described for example in U.S. Pat. Nos. 3,598,122 and 3,598,123.

In one embodiment, the system according to the invention contains a backing layer which is impervious to the active substance, a polymer matrix containing the active substance, with 2 to 10% of a weak base, a weak acid or a salt for adjusting the pH of the skin and means for securing the system to the skin.

The matrix which contains the active substance preferably consists of an emulsion-polymerised polyacrylate. Systems of this kind are disclosed for example in published German Application 2920500, European Patent Application 209121 and European Patent 86997, the contents of which are hereby referred to.

Particularly preferred emulsion polymers are the copolymers based on the alkyl esters of acrylic and methacrylic acid. The general formula is

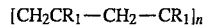

wherein $R_1$=H, $CH_3$ and $R_2$=H, $C_1$–$C_4$-alkyl $C_1$–$C_4$-alkyl-$N(C_1$–$C_4$-alkyl$)_2$.

The average molecular weight is between $6.10^4$ and $1.6$–$10^7$, the range between $10^4$ and $10^6$ being preferred.

The following Eudragit emulsion polymers

| E 30 D | MW | 800 000 | $R_1$ = H, $CH_3$, $R_2$ = $CH_3C_2H_5$; |
|---|---|---|---|
| E 12,5/100 | MW | 150 000 | $R_1$ = $CH_3$ $R_2$ = $CH_2$—$CH_2$—$N(CH_3)_2$ $CH_3$, $C_4H_9$. |
| L/S 100 | MW | 135 000 | $R_1$ = $CH_3$ $R_2$ = H, $CH_3$; | made by Röhm GmbH of Darmstadt and mixtures thereof are preferred.

In order to produce the embodiment described above having a matrix of an emulsion polymer, the following procedure is used:

The freeze dried latex is taken up in an organic solvent or mixture of solvents which is capable of dissolving both the drug and the polyacrylate. The additive for adjusting the pH on the skin is either added in finely divided form as a powder or, if the solvent is water-miscible, in the form of a solution or suspension in water. Examples of solvents include lower aliphatic alcohols, ethers, ketones, esters, hydrocarbons or halohydrocarbons, particularly those having a boiling point below 100° C. which evaporate easily. Mixtures of solvents may also be used. The viscosities of the starting solution can be varied by a suitable choice of solvent or solvent mixture. The films should normally have a thickness of about 50 to 200 μm. The temperature at which the solution dries to a film is normally from ambient temperature to, at most, the boiling temperature of the solvent or the solvent mixture used, although normally drying will be carried out at lowest possible temperatures owing to the instability of many pharmaceutically active substances and the risk of bubble formation in the film. The film may be produced or discontinuously. The films obtained are cut into suitable pieces or stamped out and packaged in the usual way for the production of transdermal preparations, possibly by applying a supporting and/or covering layer to one side of the film which contains the active substance and by attaching an adhesive layer with a removable protective coating to the other side. It may be attached to the skin using an adhesive covering plaster.

In another embodiment in which the transdermal system contains a membrane for controlling the release of active substance, the additives for adjusting the pH are provided on or in the side of the membrane facing the skin.

In another embodiment, the transdermal system takes the form of a multi-chamber system, with one or more active substances incorporated in separate chambers whilst according to the invention the additives for adjusting the pH are provided in other chambers. The additives may occur in discrete chambers, e.g. in the form of a gel, solution or suspension.

Irrespective of the nature of the matrix system, the additive for adjusting the pH may be contained in a separate layer on the side which is next to the skin.

This layer may take the form of a tackypolymer, a non-tackypolymer, a gel, e.g. an agarose gel, in the form of a (viscous) solution or in the form of small particles.

It is not absolutely necessary for the separate layer containing the additive to cover the entire active substance matrix.

The present invention also relates to a transdermal system, free from active substance, in the form of a plaster for adjusting the pH on the skin surface, characterised in that the plaster contains recesses. These plasters may be used as under-plasters for placing under any plaster which contains active substance, e.g. in order to improve the optimum flux rate of existing systems. In this case, the active substance is chiefly diffused through the surface of the skin which is not covered by the under-plaster.

In another embodiment of an under-plaster according to the invention containing no active substance, this may also be constructed so as to cover the skin completely, provided that neither its thickness nor its composition cause it to interfere with the diffusion of the active substance from the plaster containing the active substance. This is the case, for example, with thin polyacrylate films.

The composition of the under-plaster according to the invention with regard to the polymer (matrix) and the additive for adjusting the pH is analogous to that of the systems containing active substances described hereinbefore.

In another embodiment, the transdermal system contains, on the side facing the skin, small needles which pass through the stratum corneum and thus allow drugs to diffuse, unobstructed, through the pin pricks. (The "mosquito" system). The salts required keep the active substances in solution, on the one hand, so that they can penetrate through the stratum corneum into the epidermis without crystallising out, but by a suitable choice of pH, in the acid buffered range, also prevent the growth of bacteria, so as to avoid the use of preservatives on the skin which may cause reactions of intolerance. Plasters of this type for transdermal use are described for example in DE-OS 2305989.

Figure 9:
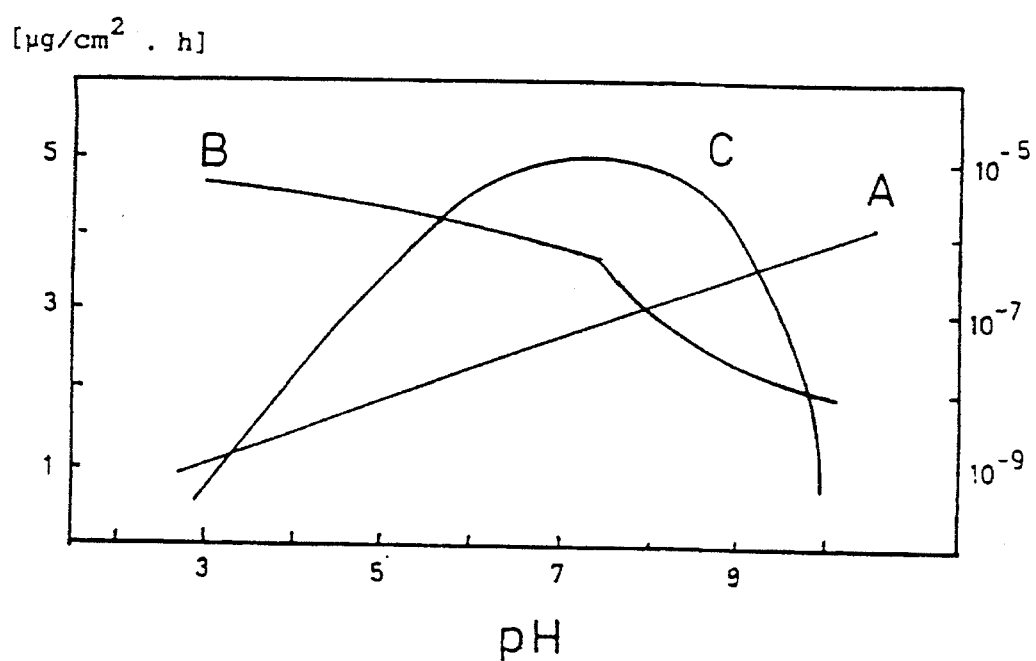
FIG. 9 is a chart showing flux rate of clenbuterol in specified pH ranges.

FIG. 9 shows the permeability P of clenbuterol through human skin (function A); P is given in [cm/sec]. Curve B illustrates the water solubility of the substance depending on the pH value [mg/ml]. Curve C shows the flux rate of clenbuterol over a wider pH range. (The right-hand ordinate in FIG. 9 is shown logarithmically). [μg/cm². h]

FIG. 1 of the drawings shows a plan view of a plaster 1 according to the invention. By contrast to what is shown in the drawing, the plaster may just as easily be rectangular or circular.

Figure 2:
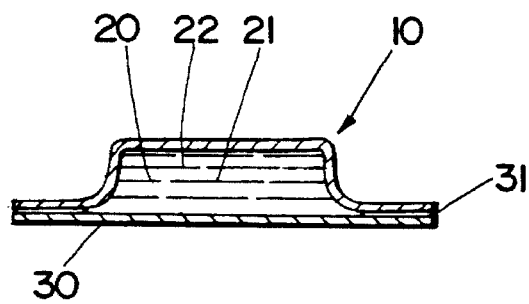
FIGS. 2, 3, 4 and 5 show cross-sectional views of transdermal patches, revealing internal structure.

FIG. 2 shows the cross section of a preferred embodiment of the plaster 10, in which the active substance 21 and the additive 22 for adjusting the pH are uniformly distributed in a polymer matrix. The protective film 30 is removed before use so as to expose the adhesive surface 31.

Figure 3:
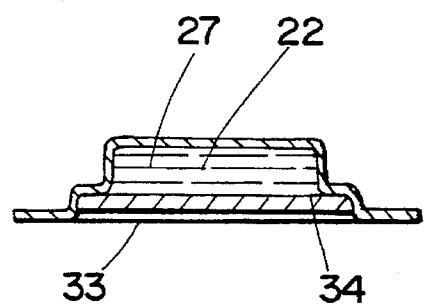

FIG. 3 shows another embodiment of the plaster 10, in which the release of active substance is controlled by a membrane 33. The additive 22 is contained in a separate layer 34. This drawing does not show the protective film 30.

Figure 4:
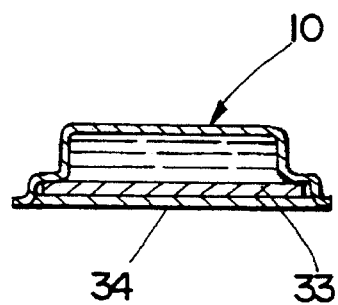

FIG. 4 Shows a similar embodiment of the plaster 10, but with the layer 34 consisting of a tackypolymer which contains the additive 22.

Figure 5:
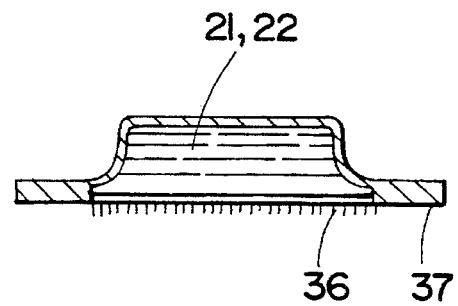

FIG. 5 shows a cross section through a plaster which has on its underside small needles for penetrating the topmost layer of skin. The polymer matrix 20 contains the active substance 21 and the additive 22. The flattened outer sides 35 of the plaster contain, on the underside, an adhesive layer 31 for fixing to the skin.

The examples which follow are intended to illustrate the invention.

Preparation Example 1

Preparation of clenbuterol-eudragit NE 30 D solution:

| | |
|---|---|
| Acetone | 1734 mg |
| is placed in a heatable container with an airtight seal, with stirring, and | |
| Clenbuterol | 21 mg |
| and | |
| Citric acid | 21 mg |
| are slowly added thereto, with stirring. | |
| Eudragit NE 30 D | 434 mg |

The heater is closed and heated to 40° C. with stirring. At this temperature, stirring is continued until a homogeneous solution has formed. The solution must be free from clusts. The viscosity of the solution should be between 3000 and 4000 mPas. The heated solution is applied by means of a direct coating apparatus consisting of applicator means, heating channel and cooling means. A fixed blade (doctor blade) is arranged at right angles to the direction of advance in the applicator means.

In front of the blade, the viscous acetone solution prepared as described above is applied to a carrier film.

The film is thus produced by a method as described in "Technologische Schriftenreihe: Veredelung bahnförmiger Materialien, Beschichten und Imprägnieren," Berger Verlag, Frankfurt.

The acetone in the cast film is evaporated either by the ambient temperature or by means of a heating channel. The coated carrier strip is cooled and then wound onto a film. Pieces of any desired size may be stamped out. The pieces are stuck into a covering plaster and can then be stuck onto the patient.

Preparation Example 2

| | |
|---|---|
| Acetone | 1734 mg |
| is placed in a heatable container, with an airtight seal, with stirring and | |
| Clenbuterol | 21 mg |
| and | |
| Sodium carbonate | 21 mg |
| are slowly added thereto with stirring. | |
| Eudragit NE 30 D | 434 mg | is added.

Processing is continued as described in Preparation Example 1, except that a suspension is formed instead of a clear solution.

EXAMPLE 1

Permeability of pH-modified clenbuterol CPA through human skin:

| Composition of the CPA's: | pH 10.0 | pH 3.5 |
|---|---|---|
| Clenbuterol | 5% | 5% |
| Citric acid | | 5% |
| $Na_2CO_3$ | 5% | |
| Polymethacrylate Eudragit ® E 30 D | 90% | 90% |

A Franz cell was used as the release apparatus. This is a conventional method of testing the release of drugs from pharmaceutical formulations. Samples were taken after 24 hours and 48 hours and the clenbuterol content was determined.

| Cell | pH-value 3.5 | | | pH-value 10.0 | | |
|---|---|---|---|---|---|---|
| | 1 | 2 | 3 | 1 | 2 | 3 |
| Clenbuterol Diffusion after 24 hours in µg/cm$^2$ | 3.48 | 0.65 | 2.64 | 7.8 | 11.44 | 9.84 |
| Clenbuterol Diffusion after 48 hours in µg/cm$^2$ | 5.52 | 1.69 | 6.04 | 21.7 | 27.3 | 24.2 |

It is clear that a higher diffusion rate is found at an alkaline pH than at an acid pH.

EXAMPLE 2

Figure 6:
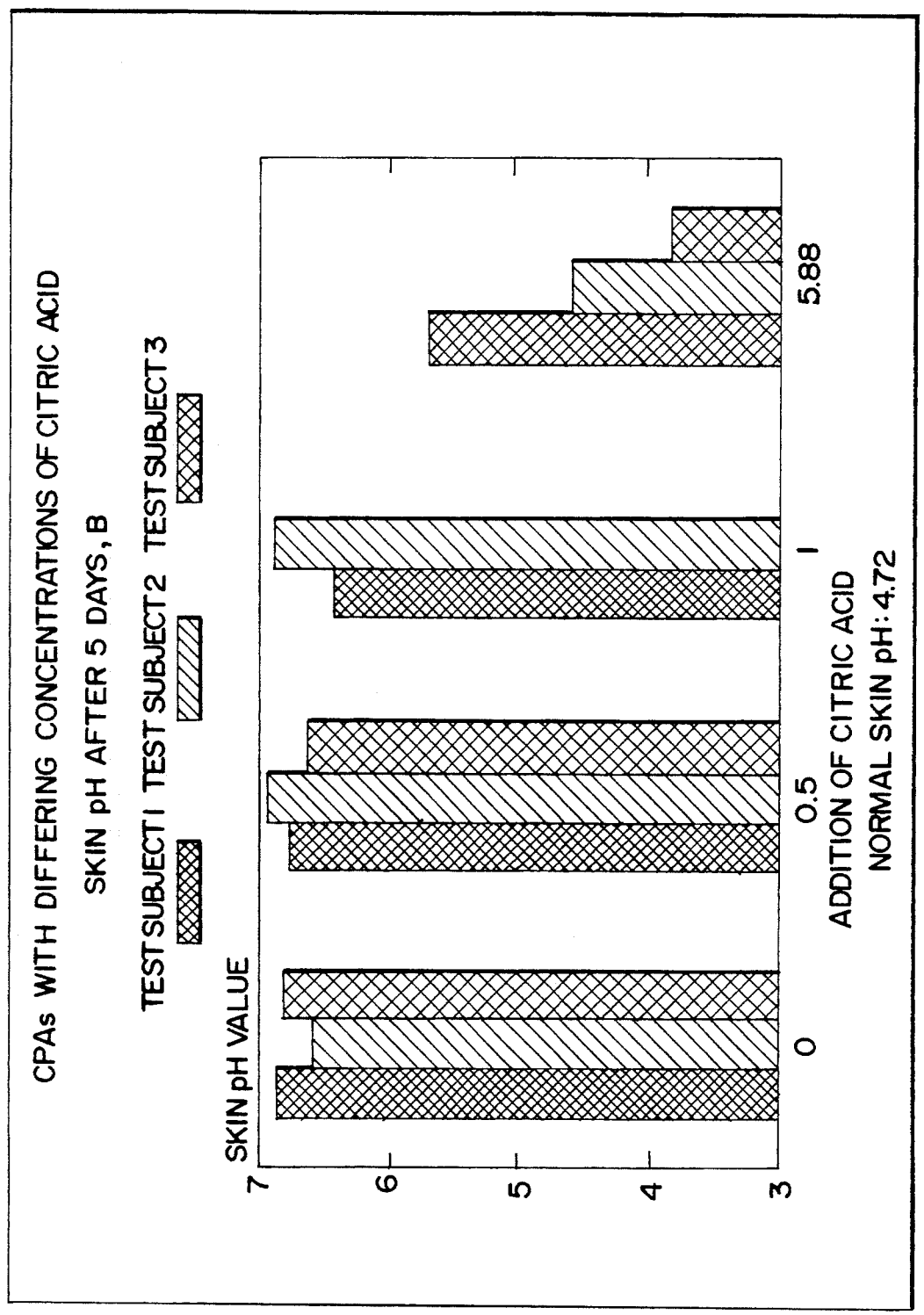
FIG. 6 is a chart of skin pH values.

FIG. 6 shows results regarding the pH of the skin surface determined underneath the system on the skin after 5 days' wearing, using a surface pH electrode. The systems tested differ in their concentration of citric acid in the polymethacrylate matrix. It is clear that only a citric acid concentration of more than 1% can bring about any significant change in the surface pH of the skin. The words "values 1, 2 and 3" in FIG. 7 refer to test subjects.

EXAMPLE 3

Figure 7:
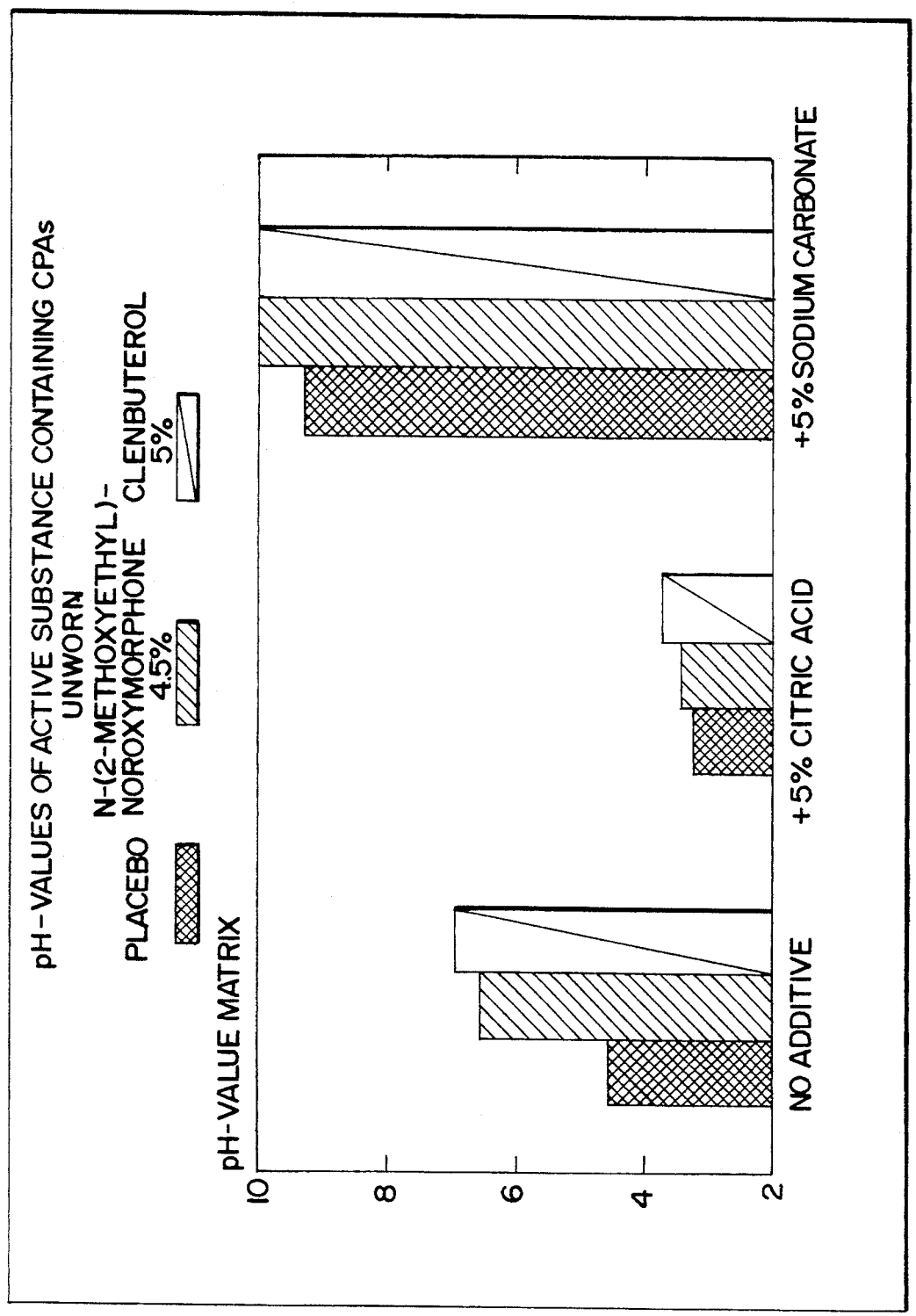
FIG. 7 is a chart of pH values of various components that can be used in transdermal patches.

FIG. 7 shows surface pH levels of drug-containing CPA's of basic active substances which were changed by the addition of 5% citric acid or Na$_2$CO$_3$. As a comparison, the surface pH found without the addition of salts or ionic substances was also determined. It is clearly apparent that the pH can be varied both to basic pH levels and to acid pH levels.

EXAMPLE 4

Figure 8:
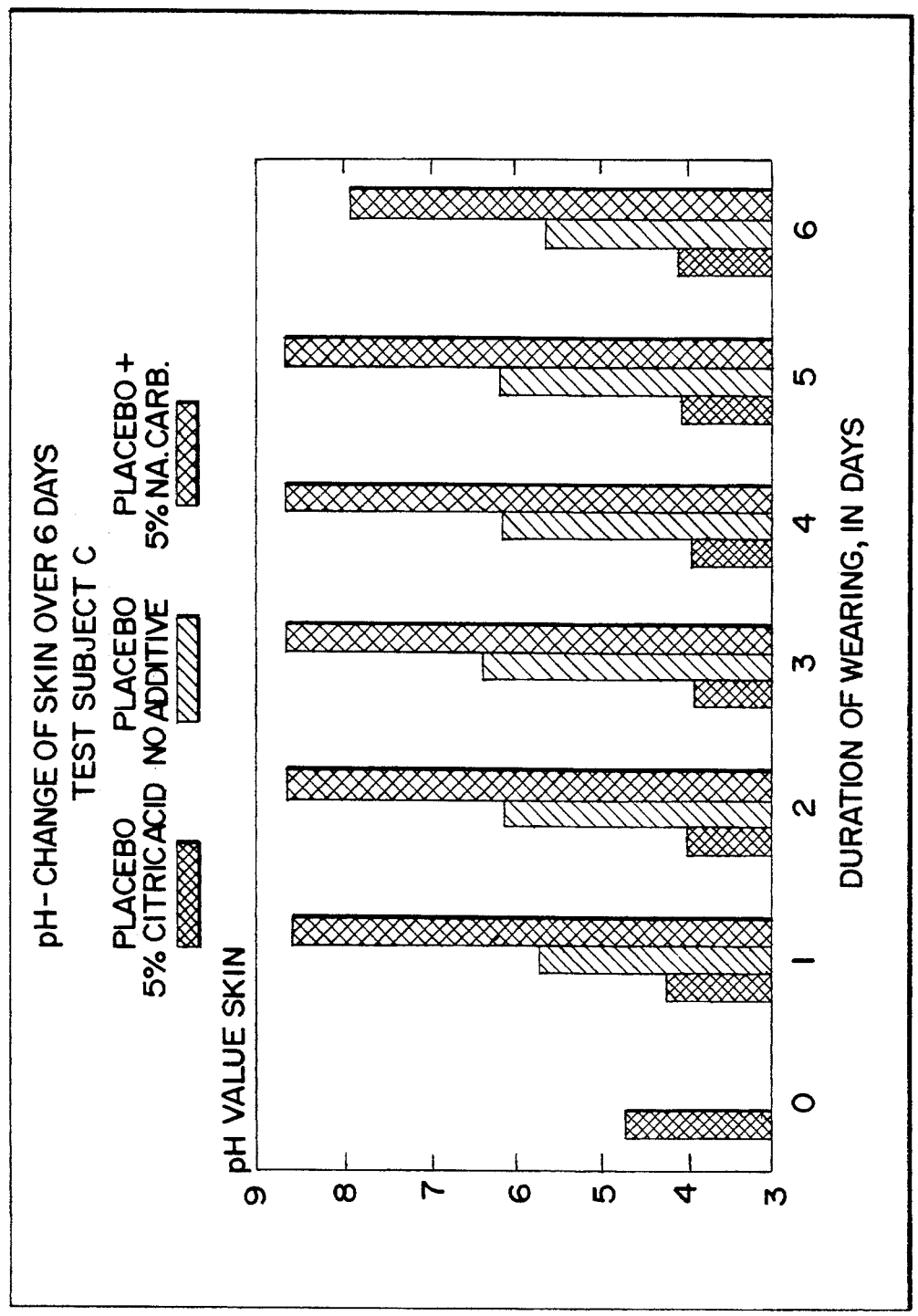
FIG. 8 is a chart of skin pH value changes over six (6) days.

FIG. 8 shows the pH on the skin under a transdermal therapeutic system applied thereto and worn for 6 days. The pH adjustments on the surface are clearly shown. The pH value selected is maintained on the skin for this period.

What is claimed is:

1. A method of administering a pharmacologically active substance via a transdermal therapeutic delivery system which comprises maintaining the pH value of the skin surface substantially constant within a predetermined pH range at which the flux rate of the active substance is at a maximum by contacting the skin surface with a pharmacologically acceptable additive comprising a weak base, a weak acid, organic or inorganic salts which form a buffering system, or mixtures thereof, which additive provides a pH of from 3 to 10.

2. The method as recited in claim 1 in which the additive is used in an amount of from 2 to 10% by weight based on the weight of active ingredient-containing therapeutic delivery system.

3. The method as claimed in claim 1 in which the active substance is clenbuterol and the pH is maintained at between 6.0 and 8.5.

4. A method of administering transdermally a pharmacologically active substance selected from the group consisting of physostigmine, clonidine, fentanyl, ephedrine, nicotinicacidamide, clenbuterol, pramipexol, lisuride, terbutaline, salbutamol, hexoprenaline, insulin, vasopressin and atrial natriuretic peptide (ANP) which comprises maintaining the pH value of the skin surface substantially constant within a predetermined range which includes the range over which the flux rate of the active substance is at a maximum by contacting the skin surface with a pharmacologically acceptable additive comprising a weak base, a weak acid, organic or inorganic salts which form a buffering system, or mixtures thereof, which additive provides a pH of from 3 to 10.

\* \* \* \* \*